Figure 1:
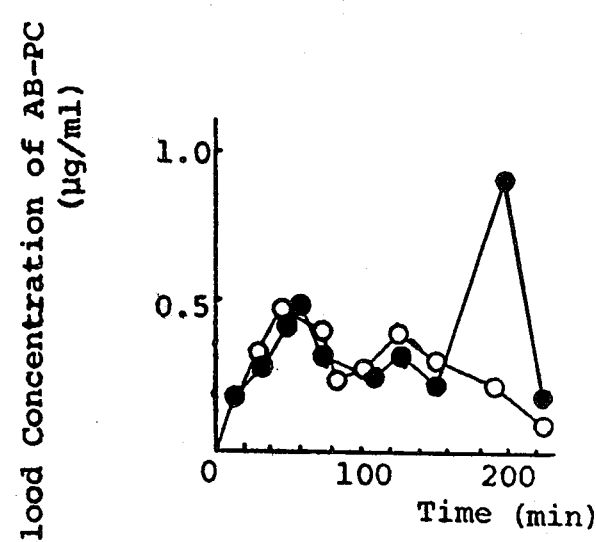

United States Patent [19]

Kamada

[11] 4,277,465
[45] Jul. 7, 1981

[54] ADJUVANT FOR PROMOTING ABSORPTION OF THERAPEUTICALLY ACTIVE SUBSTANCES THROUGH THE DIGESTIVE TRACT

[75] Inventor: Akira Kamada, Suita, Japan

[73] Assignees: Kyoto Yakuhin Kogyo Kabushiki Kaisha, Kyoto; Sawai Seiyaku Kabushiki Kaisha, Osaka, both of Japan

[21] Appl. No.: 67,451

[22] Filed: Aug. 17, 1979

[30] Foreign Application Priority Data

Aug. 26, 1978 [JP] Japan .................................. 53-104130
Jul. 30, 1979 [JP] Japan .................................. 54-97931

[51] Int. Cl.³ ............................................ A61K 37/26
[52] U.S. Cl. ............................ 424/178; 424/DIG. 15
[58] Field of Search ........................................ 424/178

[56] References Cited

U.S. PATENT DOCUMENTS 3,591,574  7/1971  Fenichel et al. ..................... 424/178

Primary Examiner—Frederick E. Waddell
Attorney, Agent, or Firm—Wenderoth, Lind & Ponack

[57] ABSTRACT

The enamine derivatives having following formula

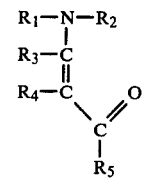

promote absorption of therapeutically active substances through the digestive tract into the blood stream and are able to effectively elevate the concentration of such active substances in the blood stream even when said active substances are usually absorbable through the digestive tract only with considerable difficulty.

13 Claims, 7 Drawing Figures

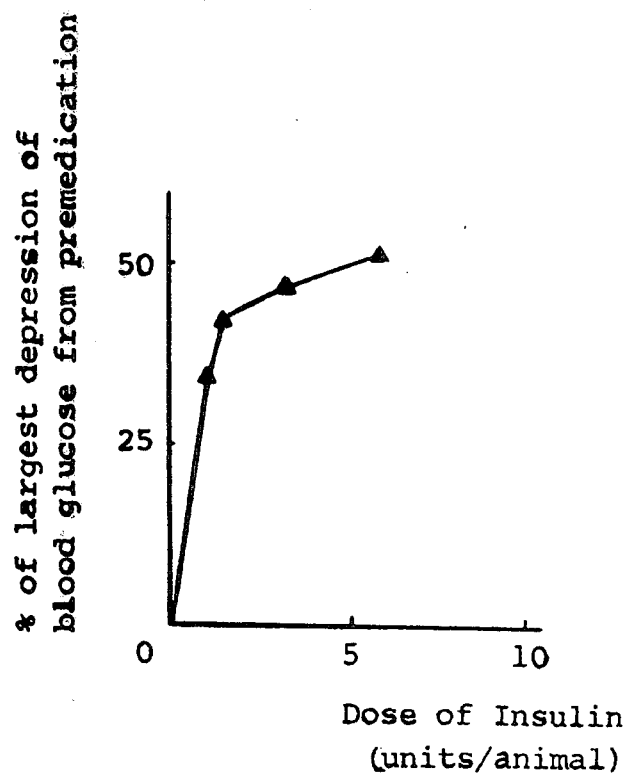
FIG. 5 Dose Response Curve
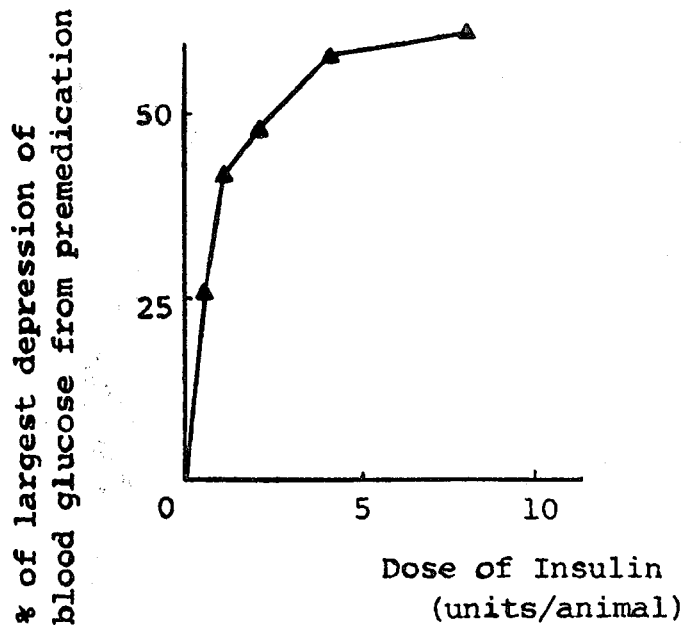
FIG. 6 Dose Response Curve

ADJUVANT FOR PROMOTING ABSORPTION OF THERAPEUTICALLY ACTIVE SUBSTANCES THROUGH THE DIGESTIVE TRACT

This invention relates to an adjuvant for promoting absorption of therapeutically active substances through the digestive tract and a pharmaceutical composition comprising a therapeutically active substance and said adjuvant, said composition being beneficial in that the therapeutically active substance contained therein is readily absorbed into the blood stream through the digestive tract even when said active substance is usually absorbable through the digestive tract only with considerable difficulty.

Several compounds have heretofore been proposed as adjuvants for promoting absorption of medicinal substances through the digestive tract, but have been found to be disadvantageous in that some are useful only for oral application while others are not efficient enough to bring about a therapeutically effective blood concentration of the concomitant active substance.

The intensive search undertaken under the above circumstances into adjuvants which would promote absorption or therapeutically active substances through the digestive tract and particularly for those substances which could be successfully employed for rectal administration has resulted in the finding that enamine derivatives of the following general formula (I) have an excellent absorption-promoting action and that a pharmaceutical composition containing such an adjuvant is capable of ensuring a high and sustained blood concentration of the therapeutically active substance concomitantly present, irrespective of the kind of therapeutically active substance or the dosage forms employed, such as suppositories, tablets, capsules or sublingual tablets, etc.

Thus, this invention relates, in one aspect, to an absorption-promoting adjuvant comprising one or more members of enamine derivatives having the general formula:

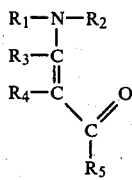

(I)

(wherein

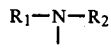

means the residue of an organic aminocarboxylic acid or organic aminosulfonic acid with a hydrogen atom removed from its amino group; the carboxyl or sulfo group of said residue being optionally in the form of an alkali metal salt or ester; $R_1$ and $R_2$ may as taken together form a ring structure; $R_3$ is hydrogen atom, lower alkyl or lower alkoxy; $R_4$ is hydrogen atom, lower alkyl or lower alkoxycarbonyl; $R_5$ is lower alkyl, lower alkoxy which may optionally be substituted by hydroxyl, carboxyl or lower alkoxycarbonyl, or lower alkylamino substituted by hydroxyl, carboxyl or lower alkoxycarbonyl; When $R_3$ and $R_4$ are both lower alkyls, the two may as taken together form a carbocyclic group; when $R_4$ is lower alkyl and $R_3$ is lower alkoxy, the two groups may as taken together form an oxygen-containing ring.)

In another aspect, this invention relates to a pharmaceutical composition comprising a therapeutically active substance and said adjuvant.

It is therefore an object of this invention to provide an adjuvant which promotes absorption of a therapeutically active substance through the digestive tract, said adjuvant comprising of one or more enamine derivatives (I).

It is another object to provide a pharmaceutical composition comprising a therapeutically active component and said absorption-promoting adjuvant. Other objects of the invention will become apparent from the following description and claims.

FIGS. 1-7 are graphs showing the effectiveness of the present invention.

Some of the enamine derivatives (I) which may be employed in accordance with this invention are novel compounds. Thus, for example, the compounds represented by the following general formula:

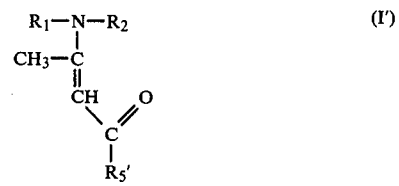

(I')

(wherein

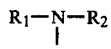

has the same meaning as defined hereinbefore; $R'_5$ is a lower alkoxy or lower alkylamino group substituted by hydroxyl, carboxyl or lower alkoxycarbonyl) are novel compounds.

Referring to

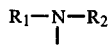

in general formula (I) and (I'), said organic aminocarboxylic acid means a carboxylic acid containing a primary or secondary amino group. Such organic aminocarboxylic acids include not only naturally-occurring alpha-amino acids but also such amino carboxylic acids as p-aminobenzoic acid, phenylglycine, etc. The naturally-occurring alpha-amino acids may be acidic, basic or neutral amino acids. Some di- and tripeptides also come under the definition of said organic aminocarboxylic acids. Thus, there may be mentioned aliphatic monoaminomonocarboxylic acids such as glycine, alanine, valine, leucine, isoleucine, etc.; aliphatic hydroxyamino acids such as serine, threonine, etc.; sulfur-containing aliphatic amino acids such as cysteine, cystine, methionine, etc.; aliphatic monoaminodicarboxylic acids such as aspartic acid, glutamic acid, etc. (inclusive of the compounds obtainable by amidating one of the carboxyl groups of such dicarboxylic acids, such as asparagine, glutamine, etc.); aliphatic diaminomonocarboxylic acids such as lysine, arginine, etc.; aromatic amino acids such as phenylalanine, tyrosine, etc.; heterocyclic amino acids such as histidine, tryptophan, proline, oxyproline, etc.; and so on. As examples of said amino carboxylic acids, which are not naturally occurring, there may be mentioned β-aminopropionic acid, γ-aminobutyric acid, anthranilic acid, p-aminobenzoic acid, etc. The carboxyl group of such organic aminocarboxylic acids may be in the form of an alkali metal salt (e.g. sodium, potassium or other salt) or an ester. The ester may for example be an alkyl ester of 1 to 6 carbon atoms, preferably one containing 1 to 4 carbon atoms (e.g. methyl, ethyl, propyl or other ester.)

The organic aminosulfonic acid means any of aliphatic, aromatic and heterocyclic sulfonic acids corresponding to said aminocarboxylic acids whose carboxyl groups have been replaced by a sulfo group.

Among such organic aminosulfonic groups are taurine and aminobenzenesulfonic acid. The sulfo group may be in the form of an alkali metal salt or an ester as mentioned in connection with said carboxyl groups.

$R_1$ and $R_2$ are such that either one of $R_1$ and $R_2$ may for example be a lower alkyl group or aryl group substituted by carboxyl and/or sulfo, and these groups may be further substituted by amino, mercapto, lower alkylamino, lower alkylthio, heterocyclic group, aryl group, etc. The other of $R_1$ and $R_2$ may usually be a hydrogen atom, although it may be lower alkyl, in which case $R_1$ and $R_2$ may as taken together form a ring structure.

In the above connection, the lower alkyl group may for example be an acyclic alkyl group of 1 to 6 carbon atoms, preferably 1 to 4 carbon atoms, such as methyl, ethyl, propyl, isopropyl, butyl, tert-butyl, pentyl, hexyl, etc.; and a cycloalkyl group of 5 to 6 carbon atoms, such as cyclopentyl and cyclohexyl. The aryl group may for example be phenyl, α-naphthyl or β-naphthyl.

The lower alkyl group $R_3$ in general formula (I) may for example be an acylic alkyl group of 1 to 6 carbon atoms, preferably 1 to 4 carbon atoms, such as methyl, ethyl, n-propyl, isopropyl, n-butyl, isobutyl, tert-butyl, pentyl, hexyl, etc. or a cycloalkyl group of 5 to 6 carbon atoms, such as cyclopentyl and cyclohexyl. The lower alkoxy which is also designated by $R_3$ may for example be an acyclic alkoxy group of 1 to 6 carbon atoms, preferably 1 to 4 carbon atoms, such as methoxy, ethoxy, n-propoxy, isopropoxy, n-butoxy, isobutoxy, tert-butoxy, pentyloxy, hexyloxy, etc. or a cycloalkoxy group of 5 to 6 carbon atoms, such as cyclopentyloxy, and cyclohexyloxy.

The lower alkyl $R_4$ in general formula (I) may be any of the lower alkyls named with reference to $R_3$. The lower alkoxy moiety of lower alkoxycarbonyl $R_4$ may be any of the lower alkoxy groups mentioned with reference to $R_3$.

The lower alkyl and lower alkoxy groups $R_5$ in general formula (I) may be the same as those mentioned with reference to $R_3$.

The above lower alkoxy group may be substituted by one or more members of the group consisting of hydroxyl, carboxyl and lower alkoxycarbonyl, etc. These substituents may be the same or different.

The lower alkoxy moiety of said lower alkoxycarbonyl group as one of the above-mentioned substituent may be the same as that defined and illustrated with reference to $R_3$. The lower alkyl moiety of lower alkylamino substituted by hydroxyl, carboxyl and/or lower alkoxycarbonyl, as designated by $R_5$, may be the same as that defined and illustrated with reference to $R_3$. This lower alkylamino group may be substituted by 2 or more substituents which may be the same or different.

The lower alkoxy moity of lower alkoxycarbonyl in said substituent may be the same as that defined and illustrated with reference to $R_3$.

When both $R_3$ and $R_4$ are lower alkyls, the compound (I) may be represented by general formula (II):

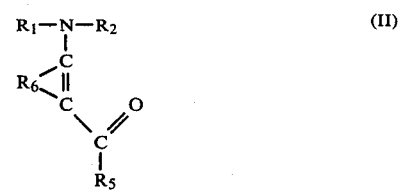
(II)

(wherein

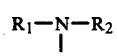

and $R_5$ are as defined hereinbefore; $R_6$ is lower alkylene)

The lower alklene group $R_6$ may be an alkylene group of 1 to 4 carbon atoms, such as methylene, propylene, butylene, etc. When, in general formula (I), $R_4$ is lower alkyl and $R_3$ is lower alkyloxy, the compound (I) may be represented by the general formula (III):

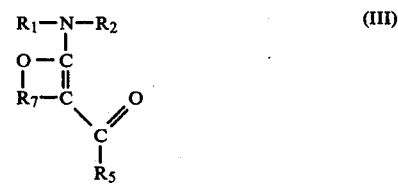
(III)

(wherein

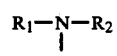

and $R_5$ are as defined hereinbefore; $R_7$ is lower alkylene)

The lower alkylene $R_7$ may for example be an alkylene group of 1 to 4 carbon atoms, such as ethylene, propylene and butylene.

Referring to general formula (I'), the lower alkoxy or lower alkylamino group $R'_5$ as substituted by hydroxyl, carboxyl and/or lower alkoxycarbonyl has the same meaning as defined with reference to $R_5$ in general formula (I).

The enamine derivative (I) according to this invention can be produced by any procedure analogous to the method described in Chemiche Berichte, 98, 789 (1965). Thus, an organic aminocarboxylic acid, an aminosulfonic acid or an alkali metal salt thereof is reacted with an acylacetate or a β-diketone at room temperature or an elevated temperature. This reaction may be written as follows.

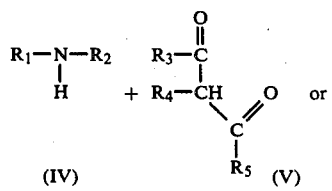
(IV) (V)

-continued

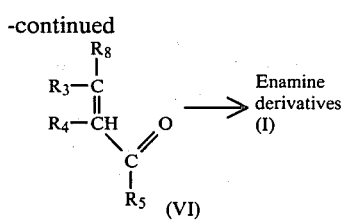

(In the above formulas,

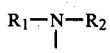

and $R_3$ to $R_5$ are as defined hereinbefore; $R_8$ is a group which is removable on reaction with an amine.)

Thus, the primary or secondary amino group in said organic aminocarboxylic acid or aminosulfonic acid (IV) reacts with the acyl-acetate or $\beta$-diketone (V) or a derivative thereof (VI) to yield the desired enamine derivative. As examples of compounds (V) and (VI), there may be mentioned acetylacetone, propionylacetone, butyroylacetone, methyl acetoacetate, ethyl acetoacetate, n-propyl acetoacetate, isopropyl acetoacetate, n-butyl acetoacetate, isobutyl acetoacetate, tert-butyl acetoacetate, n-pentyl acetoacetate, methoxyethyl acetoacetate, ethoxyethyl acetoacetate, isopropoxyethyl acetoacetate, n-propoxyethyl acetoacetate, α-acetylbutyrolactone, cyclopentanone-2-carboxylic acid methyl ester, cyclopentanone-2-carboxylic acid ethyl ester, cyclopentanone-2-carboxylic acid isopropyl ester, cyclopentanone-2-carboxylic acid n-butyl ester, cyclohexanone-2-carboxylic acid methyl ester, cyclohexanone-2-carboxylic acid ethyl ester, cyclohexanone-2-carboxylic acid propyl ester, ethoxymethylene malonic acid diethyl ester, ethoxymethylene malonic acid dipropyl ester.

This reaction is generally carried out in a solvent. Solvents which will not interfere with the reaction may be employed and, as examples, isopropyl alcohol, ether, chloroform, dioxane, benzene, ethyl acetate and toluene may be mentioned. The reaction temperature may be a mild one, e.g. room temperature to a moderately elevated temperature.

As mentioned hereinbefore, the enamine derivative (I) is employed as an adjuvant for promoting absorption of therapeutically active substances through the digestive tract. The therapeutically active substances employed in accordance with this invention may be any substances or agents which display medicinal effects when absorbed through the digestive tract of the recipient and, therefore, may cover such varied therapeutic drugs as drugs affecting the central nurvous system, antimicrobial drugs, gastrointestinal drugs, drugs affecting metabolism, cardiovascular drugs, respiratory drugs, etc. More specifically, there may be mentioned $\beta$-lactam antibiotics such as penicillins and cephalosporins, high molecular substances such as peptides, carbohydrates such as inulin, heparin, etc.. The peptides include insulin, urokinase, lysozyme and so on.

The penicillins include ampicillin, cyclacillin, cloxacillin, benzylpenicillin, carbenicillin, piperacillin, mezlocillin, pirdenicillin, ticarcillin and so on.

The cephalosporins include cephalexin cephalothin, cefoxitin, cefazolin, cephaloridine, cephacetrile, cefotiam, ceforanide and so on.

The pharmaceutical composition containing the absorption-promoting adjuvant according to this invention may assume any dosage form in which the therapeutically active substance thereof may pass into the circulation through the digestive tract. For example, oral preparations (e.g. capsules, tablets, etc.), rectal preparations (e.g. suppositories) and sublingual preparations are included. Particularly desirable are preparations for rectal administration.

Any of these dosage forms may be prepared by the established pharmaceutical procedures.

Taking rectal suppositories as an example, they may be manufactured in the following manner. First, the enamine derivative (I) is added to a suppository base and, then, a therapeutically active substance is added and dispersed. The resulting mixture is then filled and molded in a suppository container. The order of addition need not be limited to that described above but may be reversed. It is also possible to incorporate an antioxidant, preservative, volume-builder, etc. The suppository base just mentioned may be any known material, oleaginous or water-soluble. The oleaginous base includes, among others, such vegetable oils as peanut oil, olive oil, corn oil, fatty acid glyceride [e.g. Witepsol ® (Dynamite Novel Chemicals), SB-Base ® (Kanegafuchi Chemical Co., Ltd.), O.D.O ® (Nisshin Oil K.K.), etc.] and such mineral oils as paraffin and vaseline.

The water-soluble base includes polyethylene glycol, propylene glycol, glycerin, etc.

The term 'digestive tract' as used herein means any and all of the hollow organs of the body which digest and absorb and excrete the nutrients taken into the body, such as oral cavity, esophagous, stomach, small and large intestines, rectum, etc. While therapeutically active substances are generally not well absorbed when rectally administered, the presence of the adjuvant of this invention in rectal doses assists considerably in the absorption of therapeutically active substances. Therefore, this invention is especially valuable for application to rectal administration.

The level of addition of enamine derivative (I) is normally 0.5 to 85 weight %, preferably 1 to 20 W%, based on the whole preparation. More specifically, when the therapeutically active component is a $\beta$-lactam antibiotic, the concentration of enamine derivative (I) may range from 1 to 85 W%, preferably 2 to 20 W%, based on the whole preparation. In the case of insulin, the amount of enamine derivative (I) may range from 0.5 to 20 W%, preferably 1 to 15 W%.

In the case of the rectal preparations, the level of addition of therapeutically active substances is usually 0.0004 to 50 w% based on the whole preparation. More specifically, when the therapeutically active component is a $\beta$-lactam antibiotic, the concentration of $\beta$-lactam antibiotic may range from 2.5 to 50 w%, preferably from 5 to 30 w%, based on the whole preparation. In the case of insulin, the concentration of insulin (24 units/mg) may range from 0.001 to 1 w%, preferably from 0.01 to 0.5 w%. In the case of heparin, the concentration of heparin Na (100 units/mg) may range from 0.1 to 50 w%, preferably from 0.5 to 30 w%. In the case of urokinase, the concentration of urokinase (210000 units/mg) may range from 0.0004 to 0.1 w%, preferably from 0.0005 to 0.01 w%.

In the case of the oral preparations, the level of addition of therapeutically active substances is 15–99 w%, preferably 80–98 w%, based on the whole preparation, when the therapeutically active substances are β-lactam antibiotics.

Production Example 1 [Enamine derivative (I)]

The starting material aminocarboxylic acid or aminosulfonic acid sodium salt or methyl ester (0.2 M) (each of the material compounds mentioned in Table 1) was added to 50–100 ml of isopropyl alcohol, followed by addition of the acylacetate or β-diketone (0.25 M) (also listed in Table 1). The mixture was stirred at room temperature or an elevated temperature until it became a clear solution. The insolubles were then filtered off, the solvent distilled off under reduced pressure and the residue washed with petroleum ether or diethyl ether. By the above procedure were obtained the enamine derivatives (I) having molecular formula shown in Table I, Compound Nos. 1 to 4, 6 to 8 and 10 to 17, (Table 1).

Production Example 2 [Enamine derivative (1)]

The starting material aminocarboxylic acid sodium salt or methyl ester (mentioned in Table 1) (0.2 M) was reacted with diethyl ethoxymethylenemalonate (0.3 M) in 200 ml of benzene under boiling, with the byproduct ethyl alcohol being azeotropically removed.

In 3 to 5 hours, there was obtained a pale yellow solution with small amounts of crystals suspended therein. Following the above reaction, the benzene was distilled off and the residue dissolved in methanol and filtered to remove the insolubles. Then, the methanol was distilled off and the residue washed with petroleum ether or diethyl ether. By the above procedure were obtained enamine derivatives (I) having molecular formula shown in Table 1, Compound Nos. 5 and 9 (Table 1).

The elemental analyses, melting points and ultraviolet absorptions (λmax, ethanol) are given in Table 2.

1. N-(1-Methyl-2-ethoxycarbonylvinyl)glycine sodium salt (Compound 1)
2. N-(1-Methyl-2-ethoxycarbonylvinyl)-γ-aminobutyric acid sodium salt (Compound 2)
3. N-(1-Methyl-2-ethoxycarbonylvinyl)-D-phenylglycine sodium salt (Compound 3)
4. N-(1-Methyl-2-acetylvinyl)-D-phenylglycine sodium salt (Compound 4)
5. N-[2,2-bis(ethoxycarbonyl)vinyl]-D-phenylglycine sodium salt (Compound 5)
6. N-[1-(Tetrahydro-2-furanone-3-ylidene)ethyl]-D-phenylglycine sodium salt (Compound 6)
7. N-(2-Butoxycarbonyl-1-cyclopenten-1-yl)-D-phenylglycine sodium salt (Compound 7)
8. Methyl-N-(1-methyl-2-ethoxycarbonylvinyl)-D-phenylglycinate (Compound 8)
9. Methyl-N-[2,2-bis(ethoxycarbonyl)vinyl]-D-phenylglycinate (Compound 9)
10. N-(1-Methyl-2-ethoxycarbonylvinyl)-DL-phenylalanine sodium salt (Compound 10)
11. N-(1-Methyl-2-acetylvinyl)-DL-phenylalanine sodium salt (Compound 11)
12. N-[1-(Tetrahydro-2-furanone-3-ylidene)ethyl]-DL-phenylglycine sodium salt (Compound 12) 13. N-(1-Methyl-2-ethoxycarbonylvinyl)-L-proline sodium salt (Compound 13)
14. N-(1-Methyl-2-ethoxycarbonylvinyl)taurine sodium salt (Compound 14)
15. N-(1-Methyl-2-ethoxycarbonylvinyl)glycylglycine sodium salt (Compound 15)
16. N-(1-Methyl-2-ethoxycarbonylvinyl)-L-glutamic acid sodium salt (Compound 16)
17. N,N'-Bis(1-methyl-2-ethoxycarbonylvinyl)-L-lysine sodium salt (Compound 17)

TABLE 1

| Compound No. | Starting materials | | Molecular formula of products | | | | | |
| | Aminocarboxylic acid Aminosulfonic acid | Acyl acetate or β-diketone | C | H | N | O | S | Na |
| --- | --- | --- | --- | --- | --- | --- | --- | --- |
| 1 | Glycine (NA) | Ethyl acetoacetate | 8 | 12 | 1 | 4 | 0 | 1 |
| 2 | γ-Aminobutyric acid (Na) | " | 10 | 16 | 1 | 4 | 0 | 1 |
| 3 | (D) Phenylglycine (Na) | " | 14 | 16 | 1 | 4 | 0 | 1 |
| 4 | " | Acetylacetone | 13 | 14 | 1 | 3 | 0 | 1 |
| 5 | " | Ethoxy methylene malonic acid diethyl ester | 16 | 18 | 1 | 6 | 0 | 1 |
| 6 | " | α-Acetylbutyrolactone | 14 | 14 | 1 | 4 | 0 | 1 |
| 7 | " | Cyclopentanone-2-carboxylic acid butyl ester | 18 | 22 | 1 | 4 | 0 | 1 |
| 8 | (D) Phenylglycine methyl ester | Ethyl acetoacetate | 15 | 19 | 1 | 4 | 0 | 0 |
| 9 | (D) Phenylglycine methyl ester | Ethoxy methylene malonic acid diethyl ester | 17 | 21 | 1 | 6 | 0 | 0 |
| 10 | (DL) Phenylalanine (Na) | Ethyl acetoacetate | 15 | 18 | 1 | 4 | 0 | 1 |
| 11 | (DL) Phenylalanine (Na) | Acetylacetone | 14 | 16 | 1 | 3 | 0 | 1 |
| 12 | (DL) Phenylalanine (Na) | α-Acetylbutyrolactone | 15 | 16 | 1 | 4 | 0 | 1 |
| 13 | (L) Proline (Na) | Ethyl acetoacetate | 11 | 16 | 1 | 4 | 0 | 1 |
| 14 | Taurine (Na) | " | 8 | 14 | 1 | 5 | 1 | 1 |
| 15 | Glycylglycine (Na) | " | 10 | 15 | 1 | 5 | 0 | 1 |
| 16 | (L) Glutamic acid (Na) | " | 11 | 15 | 1 | 6 | 0 | 1 |
| 17 | (L) Lysine (Na) | " | 18 | 29 | 1 | 6 | 0 | 1 |

(Na): sodium salt

The chemical names of the obtained enamine derivatives (I) in Table 1 are as follows:

TABLE 2

| Compound | Calculated (%) | | | Found (%) | | | mp | λ max |
| No. | C | H | N | C | H | N | (°C.) | (nm) |
| --- | --- | --- | --- | --- | --- | --- | --- | --- |
| 1 | 45.94 | 5.78 | 6.70 | 45.86 | 5.81 | 6.82 | 168–171 | 281.0 |

TABLE 2-continued

| Compound No. | Calculated (%) C | H | N | Found (%) C | H | N | mp (°C.) | λ max (nm) |
|---|---|---|---|---|---|---|---|---|
| 2 | 50.63 | 6.80 | 5.90 | 50.65 | 6.85 | 5.96 | 110–115 | 282.5 |
| 3 | 58.95 | 5.61 | 4.91 | 58.76 | 5.70 | 5.02 | 226–227 | 289.0 |
| 4 | 61.17 | 5.53 | 5.49 | 61.22 | 5.58 | 5.61 | 124–126 | 311.0 |
| 5 | 55.98 | 5.28 | 4.08 | 56.12 | 5.32 | 4.12 | 128–129 | 283.0 |
| 6 | 59.36 | 4.98 | 4.94 | 59.28 | 5.03 | 4.99 | 159–161 | 299.5 |
| 7 | 63.71 | 6.53 | 4.13 | 63.74 | 6.62 | 4.09 | 106–109 | 299.0 |
| 8 | 64.97 | 6.91 | 5.05 | 64.12 | 6.85 | 5.11 | 98–101 | 284.5 |
| 9 | 60.89 | 6.31 | 4.18 | 60.88 | 6.34 | 4.23 | <−20 | 282.5 |
| 10 | 60.20 | 6.06 | 4.68 | 60.25 | 6.05 | 4.65 | 182–184 | 283.5 |
| 11 | 62.45 | 5.99 | 5.20 | 62.53 | 6.03 | 5.25 | 173–175 | 313.5 |
| 12 | 60.60 | 5.42 | 4.71 | 60.72 | 5.46 | 4.18 | 105–108 | 305.5 |
| 13 | 53.01 | 6.47 | 5.62 | 53.12 | 6.45 | 5.68 | >250 | 289.5 |
| 14 | 37.06 | 5.44 | 5.40 | 37.03 | 5.40 | 5.43 | 113–115 | 285.5 |
| 15 | 45.98 | 5.79 | 10.72 | 45.94 | 5.69 | 10.82 | 129–132 | 278.0 |
| 16 | 43.57 | 5.00 | 4.62 | 43.52 | 4.98 | 4.70 | 239 (dec) | 284.0 |
| 17 | 57.13 | 7.72 | 3.70 | 57.08 | 7.83 | 4.60 | 77–9 | 285.5 |

Stability in aqueous solution

To examine the stability in water of the enamine derivatives (I) obtained above, some representative compounds were selected and their half-lives [t 0.5 (min.)] in pH 7.4 phosphate buffer ($\mu$: 0.15, temp.: 25° C.) were determined by ultraviolet absorption spectrometry. The results are presented in Table 3. In the Table, "stable" means that the enamine structure was retained even after 6 hours.

TABLE 3

| Compound No. | t 0.5 (min.) | Compound No. | t 0.5 (min.) |
|---|---|---|---|
| 1 | 3.7 | 10 | 15.7 |
| 2 | 18.8 | 13 | 3.1 |
| 3 | 26.1 | 14 | 24.0 |
| 4 | Stable | 15 | 31.8 |
| 5 | Stable | 16 | 16.3 |
| 6 | 478 | 17 | 22.9 |
| 7 | Stable | | |

EXAMPLE 1

| (Recipe 1: capsule) | |
|---|---|
| Ampicillin (briefly, AB-PC) sodium | 15 mg/kg |
| Compound 3 | 10 mg/kg |

Capsules each containing the above indicated amounts of components were prepared by the conventional procedure and administrered to 3 rabbits. Immediately thereafter, each animal was given 20 ml of water and the concentration of AB-PC in the blood was measured by the biological assay method. The mean results are shown in FIG. 1. In the figure, white circles represent AB-PC alone and black circles represent the capsule according to this invention. The absorption-promoting effect of compound 3 appeared 2 to 3 hours after dosing, and in terms of the area under the blood-concentration curve (AUC: $\mu$g.min/ml), the results for each rabbit were 1.52, 1.99 and 1.73, all in excess of 1.5 times of AB-PC alone.

The blood concentrations were measured in conformity with the Antibiotic Standard of Japan. The cup method was employed with *Sarcina lutea*.

EXAMPLE 2

| (Recipe 2: solution) | |
|---|---|
| Compound 3 | 250 mg |
| Water | 20 ml |

An oral solution of the above composition was prepared according to the established pharmaceutical practice.

Figure 2:
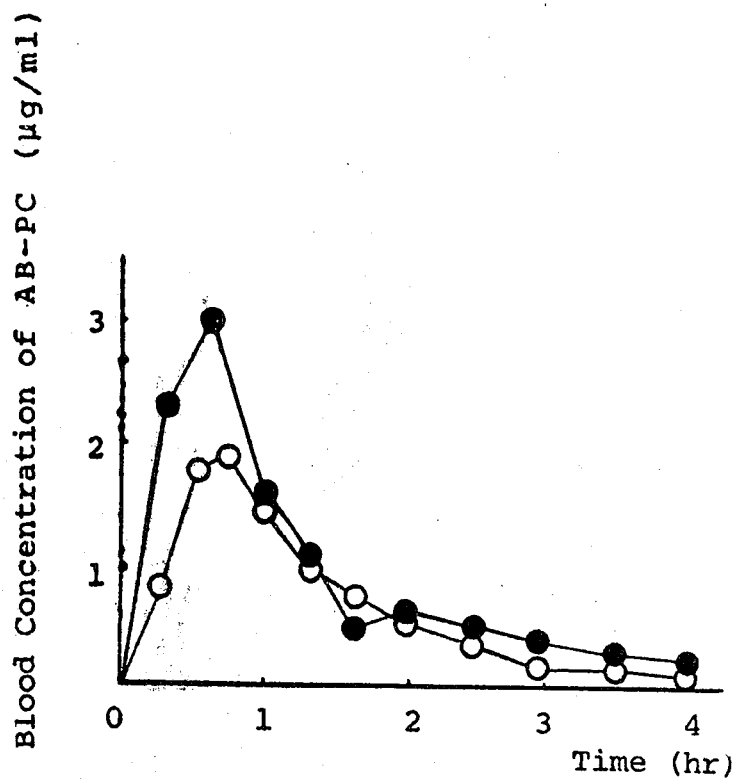

Capsules each containing 15 mg/kg of AB-PC sodium were orally administered to rabbits and immediately thereafter, the above solution was administered also by the oral route. The blood concentration of AB-PC (black circles) is shown in FIG. 2. The white circles represent AB-PC alone.

The blood concentrations were measured in conformity with the biological assay method in the Antibiotic Standard of Japan.

EXAMPLE 3

| (Recipe 3: rectal ointment) | |
|---|---|
| CET-Na | 20% |
| Compound 3 | 10% |
| Liquid paraffin | 35% |
| White vaseline | 35% |

Figure 3:
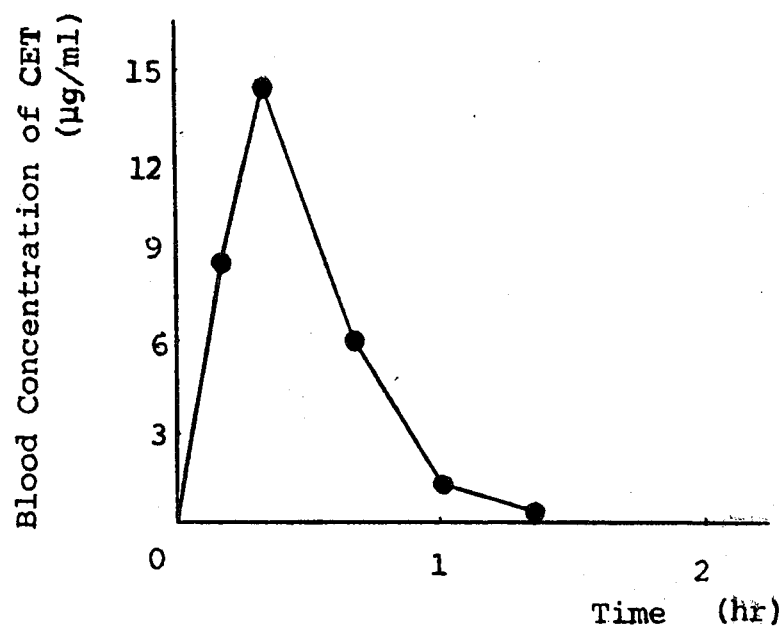

Cephalothin sodium (briefly CET-Na), a drug which is sparingly absorbed from the rectum, was selected for a test. Thus, CET-Na was dispersed in liquid paraffin-white vaseline base to prepare rectal ointment. The ointment was administered to rabbits by the rectal route. FIG. 3 shows the change in blood concentration (dose: 50 mg CET-Na/kg). A high CET level in the blood could by very quickly achieved. The blood concentration was measured in conformity with the biological assay method in the Antibiotic Standard of Japan.

EXAMPLE 4

AB-PC and cephalexin (briefly, CEX), both of which are sparingly absorbed from the rectum, are also tested. Thus, enamine derivatives (I) and these antibiotics were used to prepare rectal ointments in accordance with established practice. The ointments were administered to rabbits to investigate the peak blood concentrations ($\mu$g/ml) and AUC ($\mu$g.min./ml). The results are shown in Tables 4, 5 and 6.

| (Recipes 4 to 7: rectal ointments) | |
|---|---|
| AB-PC . Na | 10% |
| Enamine derivative (I) | 10% |
| Liquid paraffin | 40% |
| White vaseline | 40% |
| Dose: 15mg AB-PC . Na/kg | |

Compounds 3, 5, 13 and 14 were used as said enamine derivatives (I) in Recipes 4, 5, 6 and 7, respectively.

TABLE 4

| Recipe No. | Enamine derivative (I) | Peak blood concentration ($\mu$g/ml) | AUC |
|---|---|---|---|
| 4 | Compound 3 | 4.8 | 270 |
| 5 | Compound 5 | 4.7 | 149 |
| 6 | Compound 13 | 2.6 | 108 |

TABLE 4-continued

| Recipe No. | Enamine derivative (I) | Peak blood concentration (μg/ml) | AUC |
|---|---|---|---|
| 7 | Compound 14 | 5.9 | 239 |

| (Recipes 8 and 9: rectal ointments) | |
|---|---|
| CEX . H₂O | 20% |
| Enamine derivative (I) | 10% |
| Liquid paraffin | 35% |
| White vaseline | 35% |
| Dose: 50 mg CEX . H₂O/kg | |

TABLE 5

| Recipe No. | Enamine derivative (I) | Peak blood concentration (μg/ml) | AUC |
|---|---|---|---|
| 8 | Compound 2 | 6.7 | 278 |
| 9 | Compound 13 | 6.5 | 733 |

| (Recipes 10–17: rectal ointments) | |
|---|---|
| CET . Na | 20% |
| Enamine derivative (I) | 10% |
| Liquid paraffin | 35% |
| White vaseline | 35% |
| Dose: 50mg CET . Na/kg | |

TABLE 6

| Recipe No. | Enamine derivative (I) | Peak blood concentration (μg/ml) | AUC |
|---|---|---|---|
| 9 | Compound 2 | 6.3 | 315 |
| 10 | Compound 3 | 14.4 | 445 |
| 11 | Compound 4 | 11.0 | 568 |
| 12 | Compound 5 | 6.1 | 306 |
| 13 | Compound 8 | 3.8 | 49 |
| 14 | Compound 13 | 2.5 | 25 |
| 15 | Compound 14 | 7.8 | 250 |
| 16 | Compound 15 | 1.8 | 102 |
| 17 | Compound 17 | 8.7 | 396 |

EXAMPLE 5

The absorption-promoting effect of the enamine derivative (I) on β-lactam antibiotics has been confirmed in the above experiments. Then, to examine similar effects on drugs having higher molecular weights, insulin which has a molecular weight of 6000 was selected.

| (Recipe 18: rectal suppository) | |
|---|---|
| Amorphous insulin | 3 I.U. |
| Compound 3 | 0.05g |
| Witepsol H-15 ® | 0.45g |
| (Recipe 19: rectal suppository) | |
| Amorphous insulin | 1 I.U. |
| Compound 3 | 0.05g |
| Witepsol H-15 ® | 0.45g |

Figure 4:
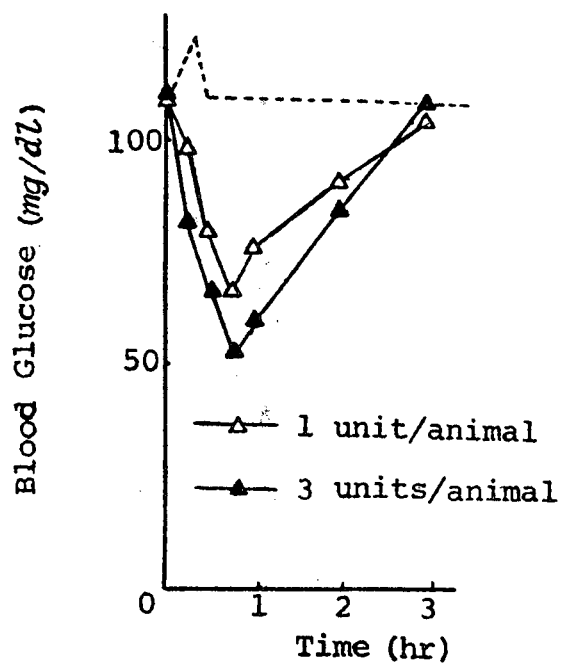

The blood glucose concentration observed after rectal administration of the above suppository to rabbits (body weights: 2.0–2.5 kg) is presented in FIG. 4.

The test was conducted by the glucoseoxidase method. The broken line represents the control glucose level (insulin alone added to base). In this case, there has been no absorption of insulin. The white triangles represent the glucose level observed after administration of one I.U. of insulin per animal, while black triangles represent the level after administration of 3 I.U. of insulin per animal. Especially in the latter case, the blood glucose concentration is reduced about 50% from the pre-medication level. The largest depression of blood glucose from the pre-medication level was expressed in % response. The results are shown in FIG. 5. The dose response curve when insulin alone was intramuscularly administered is shown in FIG. 6. The absorption-promoting effect of the adjuvant of this invention was almost comparable to the effect of intramuscular injection.

EXAMPLE 6

| (Recipe 20 - rectal suppository) To investigate the versatility of the absorption-promoting action of the adjuvant according to this invention, inulin (mol. wt. 5000) was selected as a test polysaccharide. | |
|---|---|
| Inulin | 0.25g |
| Compound 3 | 0.05g |
| Witepsol H-15 ® | 0.425g |

The above components were used to prepare a suppository in accordance with established pharmaceutical practice. The suppository was rectally administered to rabbits (body weights 2.0–2.5 kg) and the blood concentrations were determined.

Figure 7:
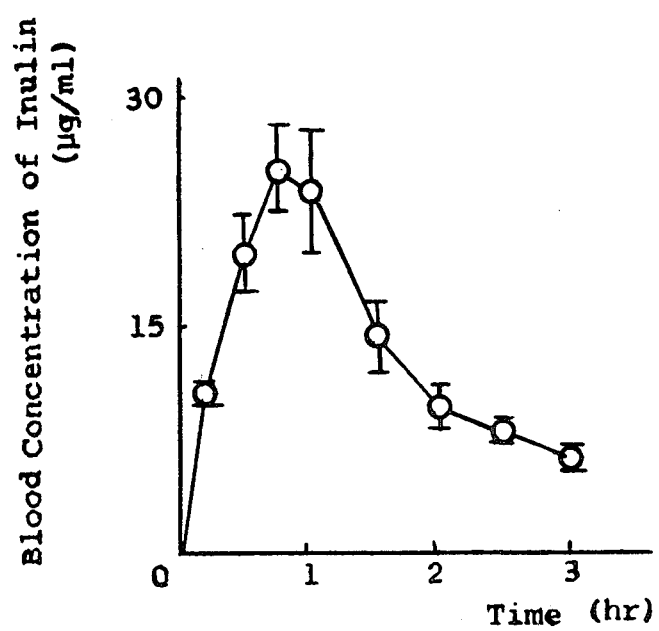

The results, shown in FIG. 7, indicates the versatility of enamine derivative (I). The amount of inulin excreted in the urine was 18% of the dose administered.

The following dosage forms (dispersed in Witepsol H-15 ®) were rectally administered to dogs and humans to measure the urinary recovery rates of inulin. The results were comparable to those obtained in rabbits (Table 7). The test was carried out by the Lunt method.

TABLE 7

| Subject | Dose of inulin | Level of addition of Enamine derivative (I) | | % Urinary recovery |
|---|---|---|---|---|
| Rabbit | mg/body | Compound 3 | 10% | 8% |
| Dog | " | " | 5% | 20% |
| Human | " | " | 1% | 11% |
| Human | " | Compound 1 | 2% | 12% |

Production Example 3 [Enamine derivative (I)]

The material amino acids or sodium salts thereof indicated in Table 8 were dissolved or suspended in the solvents also indicated in the same table. The resultant solutions or suspensions were each stirred at room temperature or an elevated temperature. Then, an equimolar amount of ethyl acetoacetate was added dropwise and the mixture was stirred for 2 to 10 hours. The solvent was distilled off under reduced pressure and the solid residue was washed or recrystallized. By the above procedure were obtained the contemplated products. The physical properties of these products are shown in Tables 9, 10 and 11.

TABLE 8

| | Material amino acid or sodium salt thereof | Solvent | Temperature | Yield (%) |
|---|---|---|---|---|
| 18 | DL-Alanine (Na) | methanol | room | 64.5 |
| 19 | L-Alanine (Na) | " | " | 60.0 |

TABLE 8-continued

| | Material amino acid or sodium salt thereof | Solvent | Temperature | Yield (%) |
|---|---|---|---|---|
| 20 | L-Isoleucine (Na) | " | " | 75.0 |
| 21 | L-Leucine (Na) | " | " | 60.0 |
| 22 | L-Threonine (Na) | " | " | 70.0 |
| 23 | L-Methionine (Na) | " | " | 72.0 |
| 24 | DL-Phenylglycine (Na) | " | " | 88.0 |
| 25 | L-Phenylalanine (Na) | " | " | 97.0 |
| 26 | L-Valine (Na) | " | 60–80° C. | 98.4 |
| 27 | L-Tryptophan (Na) | " | " | 96.8 |
| 28 | L-Histidine (Na) | ethanol | room | 97.8 |
| 29 | L-Arginine | " | 60–80° C. | 80.5 |
| 30 | 11-Aminoundecanoic acid (Na) | " | " | 84.3 |
| 31 | L-Serine (Na) | " | room | 80.5 |

(Na): Sodium salt

The following contemplated compounds were obtained.

18. N-(1-Methyl-2-ethoxycarbonylvinyl)-DL-alanine sodium salt (Compound 18)
19. N-(1-Methyl-2-ethoxycarbonylvinyl)-L-alanine sodium salt (Compound 19)
20. N-(1-Methyl-2-ethoxycarbonylvinyl)-L-isoleucine sodium salt (Compound 20)
21. N-(1-Methyl-2-ethoxycarbonylvinyl)-L-leucine sodium salt (Compound 21)
22. N-(1-Methyl-2-ethoxycarbonylvinyl)-L-threonine sodium salt (Compound 22)
23. N-(1-Methyl-2-ethoxycarbonylvinyl)-L-methionine sodium salt (Compound 23)
24. N-(1-Methyl-2-ethoxycarbonylvinyl)-DL-phenylglycine sodium salt (Compound 24)
25. N-(1-Methyl-2-ethoxycarbonylvinyl)-L-phenylalanine sodium salt (Compound 25)
26. N-(1-Methyl-2-ethoxycarbonylvinyl)-L-valine sodium salt (Compound 26)
27. α-N-(1-Methyl-2-ethoxycarbonylvinyl)-L-tryptophan sodium salt (Compound 27)
28. α-N-(1-Methyl-2-ethoxycarbonylvinyl)-L-histidine sodium salt (Compound 28)
29. α-N-(1-Methyl-2-ethoxycarbonylvinyl)-L-arginine (Compound 29)
30. N-(1-Methyl-2-ethoxycarbonylvinyl)-11-aminoundecanoic acid sodium salt (Compound 30)
31. N-(1-Methyl-2-ethoxycarbonylvinyl)-L-serine sodium salt (Compound 31)

TABLE 9

| Compound No. | mp. (°C.) | Specific rotation values $[\alpha]_D$ |
|---|---|---|
| 18 | 71–75 (dec) | 0 (H₂O 23°) |
| 19 | 157–159 (dec) | +187.0 (H₂O 23°) |
| 20 | 166–167 (dec) | +152.0 (H₂O 26°) |
| 21 | 147–149 | +115.0 (H₂O 23°) |
| 22 | 183–187 (dec) | +142.0 (H₂O 23°) |
| 23 | 108–110 | +9.0 (H₂O 23°) |
| 24 | 199–201 (dec) | 0 (H₂O 23°) |
| 25 | 96.0–97.5 | −262.5 (Absolute alcohol 23°) |
| 26 | 60.0–65.0 | +125.0 (Methanol 29°) |
| 27 | 118–120 (dec) | −260.0 (Methanol 29°) |
| 28 | 110–112 (dec) | −135.0 (Absolute alcohol 24°) |
| 29 | 120 | +52.0 (Methanol 29°) |
| 30 | 180–190 (dec) | — |
| 31 | 193–194 (dec) | +110.0 (H₂O 24°) |

TABLE 10

| Compound No. | $UV_{(m\mu)}^{(\lambda\ max,\ ethanol)}$ | $IR_{(cm^{-1})}^{(Nujol)}$ |
|---|---|---|
| 18 | 287 | 1630, 1570 |
| 19 | 387 | 1630, 1570 |
| 20 | 290 | 1640, 1620, 1580 |
| 21 | 288 | 1640, 1560 |
| 22 | 288 | 1650, 1610, 1570 |
| 23 | 288 | 1630, 1590 |
| 24 | 286 | 1640, 1560 |
| 25 | 288 | 1630, 1610, 1580 |
| 26 | 288 | 1640, 1590 |
| 27 | 284, 290 | 1630, 1580 |
| 28 | 287 | 1640, 1590 |
| 29 | 286 | 1630, 1570 |
| 30 | 284 | 1640, 1560 |
| 31 | 287 | 1660, 1650, 1620, 1570 |

TABLE 11

| Compound No. | $H_A$ | | $H_B$ | | $H_C$ | |
|---|---|---|---|---|---|---|
| 18 | 9.00 | (d,9,1$^H$) | 1.85 | (s,3$^H$) | 4.20 | (a,1$^H$) |
| 19 | 8.96 | (d,8,1$^H$) | 1.85 | (s,3$^H$) | 4.20 | (s,1$^H$) |
| 20 | 8.90 | (d,9,1$^H$) | 1.80 | (s,3$^H$) | 4.20 | (s,1$^H$) |
| 21 | 8.70 | (d,9,1$^H$) | 1.80 | (s,3$^H$) | 4.15 | (s,1$^H$) |
| 22 | 8.87 | (d,8,1$^H$) | 1.86 | (s,3$^H$) | 4.22 | (s,1$^H$) |
| 23 | 8.85 | (d,8,1$^H$) | 1.85 | (s,3$^H$) | 4.20 | (s,1$^H$) |
| 24 | 9.50 | (d,6,1$^H$) | 1.60 | (s,3$^H$) | 4.22 | (s,1$^H$) |
| 25 | 8.85 | (d,9,1$^H$) | 1.46 | (s,3$^H$) | 4.10 | (s,1$^H$) |
| 26 | 8.95 | (d,9,1$^H$) | 1.85 | (s,3$^H$) | 4.25 | (s,1$^H$) |
| 27 | 8.95 | (d,9,1$^H$) | 1.45 | (s,3$^H$) | 4.05 | (s,1$^H$) |
| 28 | 8.85 | (d,9,1$^H$) | 1.60 | (s,3$^H$) | 4.12 | (s,1$^H$) |
| 29 | 8.85 | (d,9,1$^H$) | 1.85 | (s,3$^H$) | 4.25 | (s,1$^H$) |
| 30 | — | (disappear) | 1.75 | (s,3$^H$) | 4.35 | (s,1$^H$) |
| 31 | 9.00 | (d,7,1$^H$) | 1.80 | (s,3$^H$) | 4.25 | (s,1$^H$) |
| | | | | | | (ppm) |

(Note)
1. The solvent was DMSO-d₆, except that D₂O was used for Compound 30.

2. 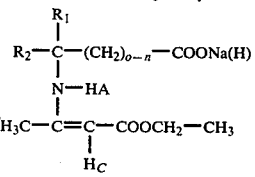

EXAMPLE 7

(Recipes 21–34: rectal suppositories)

| | |
|---|---|
| Amorphous insulin | 6 I.U. |
| Enamine derivative (I) | As indicated in Table 12 |
| Witepsol H-15 ® | To make a total of 0.5g |

The above components were used to prepare rectal suppositories in accordance with established pharmaceutical practice. The suppositories were administered to rabbits and dogs by rectal route.

Table 12 shows the glucose responses (%) obtained with the above suppositories. The test was conducted by the glucose oxidase method.

TABLE 12

| Level of addition of enamine derivative (I) | | Kind of animal | Blood glucose response (6 I.U.) (%) | Time course (min.) | | |
|---|---|---|---|---|---|---|
| | | | | Onset | Lowest level | Return to premedication level |
| Compound 18, | 1% | R | 45–55 | 30 | 45–60 | 180 |
| Compound 19, | 1% | R | 45–55 | 30 | 45–60 | 180 |
| Compound 20, | 2% | D | 25–35 | 60–90 | 120 | 180–240 |
| Compound 21, | 1% | D | 35–45 | 30 | 60–90 | 180 |
| Compound 22, | 5% | R | 40–50 | 30 | 45–75 | 180 |
| Compound 23, | 10% | R | 30 | 30 | 60–90 | 180 |
| Compound 24, | 1% | R | 50–65 | 15 | 30–60 | 180 |
| Compound 25, | 1% | R | 50–65 | 30 | 45–90 | 180 |
| Compound 26, | 10% | R | 30 | 30 | 60–90 | 180 |
| Compound 27, | 10% | R | 30 | 30 | 60–90 | 180 |
| Compound 28, | 10% | R | 30 | 30 | 60–90 | 180 |
| Compound 29, | 5% | R | 40–50 | 15 | 60–90 | 210 |
| Compound 30, | 10% | R | 30 | 30 | 60–90 | 180 |
| Compound 31, | 10% | R | 30 | 30 | 60–90 | 180 |

(Note)
R: rabbit
D: dog

Production Example 4 [Enamine derivatives (I)]

The amino acids and starting compounds (V) indicated in Table 13 were reacted under the conditions also indicated in the same table. The reaction was carried out in homogenous solution or suspension for 2 to 10 hours.

The reaction was conducted at room temperature or an elevated temperature, with constant stirring. The solvent was then distilled off and the solid residue was recrystallized to obtain the contemplated enamine derivative.

TABLE 13

| No. | Material amino acid | Material compound (V)* ($R_5$ in formula V) | Solvent | Temperature |
|---|---|---|---|---|
| 32 | Glycine (Na) | —O—CH(CH$_3$)—COOC$_2$H$_5$ | Ethanol | Room |
| 33 | DL-Alanine (Na) | —O—CH(CH$_3$)—COOC$_2$H$_5$ | Ethanol | Reflux |
| 34 | L-phenylalanine (Na) | —O—CH(CH$_3$)—COOC$_2$H$_5$ | Ethanol | Room |
| 35 | L-arginine | —O—CH(CH$_3$)—COOH | H$_2$O | Room |
| 36 | L-phenylalanine (Na) | —NHCH$_2$CH$_2$(OH) | Methanol | Room |
| 37 | L-phenylalanine (Na) | —NHCH$_2$(COOC$_2$H$_5$) | Ethanol | Room |
| 38 | Glycine (Na) | —O—CH$_2$—CH(OH)—CH$_2$OH | Ethanol | Room |

(Note)
*$R_3$ = CH$_3$, $R_4$ = H
(Na): Sodium salt

The chemical names of enamine derivatives (I) thus obtained are as follows.

32. N-[1-Methyl-2-(1-ethoxycarbonyl-ethoxycarbonyl)vinyl]glycine sodium salt (Compound 32)
33. N-[1-Methyl-2-(1-ethoxycarbonyl-ethoxycarbonyl)vinyl]-DL-alanine sodium salt (Compound 33)
34. N-[1-Methyl-2-(1-ethoxycarbonyl-ethoxycarbonyl)vinyl]-L-phenylalanine sodium salt (Compound 34)
35. α-N-(1-Methyl-2-(1-carboxy-ethoxycarbonyl)-vinyl]-L-arginine (Compound 35)
36. N-[1-Methyl-2-(2-hydroxyethylcarbamoyl)vinyl]-L-phenylalanine sodium salt (Compound 36)
37. N-(1-Methyl-2-ethoxycarbonylmethylcarbamoyl-vinyl)-L-phenylalanine sodium salt (Compound 37)
38. N-[1-Methyl-2-(2,3-dihydroxypropoxycarbonyl)-vinyl]glycine sodium salt (Compound 389

The melting points, UV spectra, IR spectra and specific rotation values of these product compounds are shown in Table 14.

TABLE 14

| Compound No. | mp. (°C.) | UV ($\lambda_{max}$) mμ (95% ethanol) | IR (cm$^{-1}$) | Specific rotation value [α]$_D$ (Ethanol 20° C.) |
|---|---|---|---|---|
| 32 | — | 288 | 1725 1640 1580 | — |
| 33 | — | 288 | 1730 1640 1580 | — |
| 34 | — | 292 | 1730 1640 1580 1640 | — |
| 35 | — | 286.5 | 1570 1620 | +34° |
| 36 | 129–135 | 287 | 1580 1610 | −183.7° |
| 37 | 101–104 | 288 | 1580 | −218.9° |

The NMR spectra of Compound 32 through 37 are as follows.

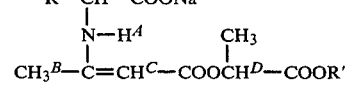 (Compound 32-35)

TABLE 15

| Compound No. | R' | $H^A$ | $H^B$ | $H^C$ | $H^D$ | Solvent |
|---|---|---|---|---|---|---|
| 32 | $C_2H_5$ | 8.72 (t,J=5,1H) | 1.85 (s,3H) | 4.30 (s,1H) | 4.82 (q,J=7,1H) | DMSO |
| 33 | $C_2H_5$ | 8.90 (d,J=7,1H) | 1.87 (s,3H) | 4.23 (s,1H) | 4.81 (q,J=7,1H) | " |
| 34 | $C_2H_5$ | 8.80 (d,J=8,1H) | 1.50 (s,3H) | 4.15 (s,1H) | 4.82 (q,J=7,1H) | " |
| 35 | H | | 1.90 (s,3H) | | 4.82 (q,J=7,1H) | $D_2O$ |

(Compound 36)

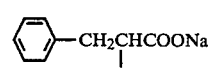
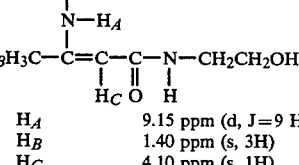

$H_A$   9.15 ppm (d, J=9 Hz, 1H)
$H_B$   1.40 ppm (s, 3H)
$H_C$   4.10 ppm (s, 1H)

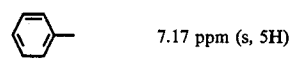   7.17 ppm (s, 5H)

(Compound 37)

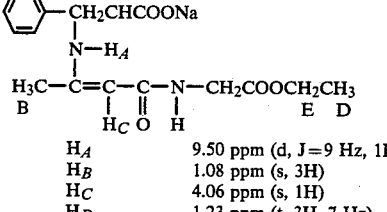

$H_A$   9.50 ppm (d, J=9 Hz, 1H)
$H_B$   1.08 ppm (s, 3H)
$H_C$   4.06 ppm (s, 1H)
$H_D$   1.23 ppm (t, 3H, 7 Hz)
$H_E$   4.10 ppm (q, 2H, 7 Hz)

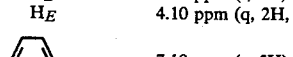   7.10 ppm (s, 5H)

EXAMPLE 8

| (Recipe 35-41: rectal suppositories) | |
|---|---|
| Amorphous insulin | 6 I.U. |
| Enamine derivative (I) | 0.025g |
| Wetspsol H-15 ® | 0.475g |

The above components were used to prepare rectal suppositories in accordance with established pharmaceutical practice. These suppositories were rectally administered to rabbits (R, 2.5-3kg) and dogs (D, 12-13kg). The glucose responses (%) and time courses (min.) are shown in Table 16.

TABLE 16

| | | Blood glucose response (6 I.U.) (%) | Time course (min.) | | |
|---|---|---|---|---|---|
| Level of addition of enamine derivative (I) | Kind of animal | | Onset | Lowest level | Return to premedication level |
| Compound 32, 5% | R | 45-55 | 15 | 45-60 | 150 |
| Compound 32, 5% | D | 30-40 | 30 | 30-60 | 120 |
| Compound 33, 5% | R | 45-55 | 15 | 45-60 | 150 |
| Compound 34, 5% | R | 45-55 | 15 | 45-60 | 150 |
| Compound 35, 5% | R | 20-30 | 15 | 30-60 | 120 |
| Compound 36, 5% | R | 20-30 | 15 | 30-60 | 120 |
| compound 37, 5% | R | 20-30 | 30 | 30-60 | 120 |
| Compound 38, 5% | R | 45-55 | 15 | 45-60 | 150 |

R: Rabbit
D: Dog

EXAMPLE 9

Suppositories were prepared in accordane with established pharmaceutical practice, using the recipes shown in Table 17. These suppositories were rectally administered to dogs and the absorbabilities of the active components were investigated by measuring the blood concentrations. The results are shown in Table 17.

The blood concentrations were measured in conformity with the biological assay method in the Antibiotic Standard of Japan. The cup method was employed with *Sarcina lutea* for penicillins and *Bacillus subtilis* for cephalosporins.

TABLE 17

| Recipe | | | | Concentration in blood (μg/ml) | | | |
|---|---|---|---|---|---|---|---|
| Enamine derivative (I) | Antibiotics | base | Body weight (Dog) (kg) | 15 min. | 30 min. | 60 min. | 120 min. |
| Compound 1 60mg (50%) | AB-PC-Na 75mg | SB-W 1065mg | 13.5 | 1.23 | 0.87 | 0.61 | 0.32 |
| Compound 10 150mg (10%) | CET-Na 500mg | Witepsol H-15 850mg | 12.0 | 15.30 | 11.73 | 6.75 | 2.20 |
| Compound 20 150mg (10%) | CET-Na 500mg | Witepsol H-15 850mg | 9.8 | 9.00 | 6.23 | 2.91 | 1.00 |
| Compound 22 60mg (5%) | CET-Na 75mg | Witepsol H-15 1065mg | 9.5 | 0.75 | 0.57 | 0.31 | — |
| Compound 27 120mg (10%) | AB-PC-Na 75mg | SB-W 1005mg | 11.4 | 1.6 | 1.5 | 0.74 | 0.40 |
| Compound 23 60mg (5%) | AB-PC-Na 75mg | Witepsol H-15 1065mg | 13.0 | 0.52 | 0.34 | 0.18 | 0.08 |
| Compound 28 60mg (5%) | AB-PC-Na 75mg | SB-W 1065mg | 10.5 | 0.56 | 0.44 | 0.14 | — |
| Compound 29 | AB-PC-Na | SB-W | 11.5 | 0.50 | 0.53 | 0.61 | 0.41 |

TABLE 17-continued

| Recipe Enamine derivative (I) | Antibiotics | base | Body weight (Dog) (kg) | Concentration in blood (μg/ml) | | | |
|---|---|---|---|---|---|---|---|
| | | | | 15 min. | 30 min. | 60 min. | 120 min. |
| 120mg (10%) | 75mg | 1005mg | | | | | |
| Compound 16 120mg (10%) | AB-PC-Na 75mg | SB-W 1005mg | 13.0 | 0.69 | 0.48 | 0.52 | 0.29 |
| Compound 31 60mg (5%) | AB-PC-Na 75mg | Witepsol H-15 1065mg | 11.3 | 0.70 | 0.38 | 0.24 | 0.09 |
| Compound 32 60mg (5%) | CET-Na 75mg | SB-W 1065mg | 11.5 | 1.50 | 1.12 | 0.73 | 0.40 |
| Compound 34 60mg (5%) | CET-Na 75mg | Witepsol H-15 1065mg | 9.5 | 1.25 | 0.83 | 0.61 | 0.39 |
| Compound 36 120mg (10%) | AB-PC-Na 75mg | Witepsol H-15 1005mg | 12.0 | 1.45 | 1.53 | 0.80 | 0.40 |
| Compound 37 120mg (10%) | CET-Na 75mg | Witepsol H-15 1005mg | 12.5 | 1.50 | 1.28 | 0.87 | 0.44 |

Na: Sodium salt

What is claimed is:

1. A pharmaceutical composition for absorption through the digestive tract, which comprises a therapeutically effective amount of insulin and an absorption promoting amount of an enamine derivative of the formula

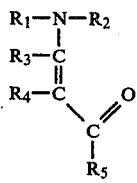

wherein

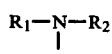

is the residue of an organic aminocarboxylic acid or organic aminosulfonic acid having a hydrogen atom removed from the amino group thereof, the carboxyl or sulfo group in said residue being optionally in the form of an alkali metal salt or ester; wherein one of $R_1$ and $R_2$ is a carboxy or sulfo substituted alkyl of 1 to 6 carbon atoms, cycloalkyl of 5 to 6 carbon atoms, phenyl or naphthyl group and the other of $R_1$ and $R_2$ is hydrogen, lower alkyl or phenyl, $R_3$ is a hydrogen atom, a lower group or a lower alkoxy group, $R_4$ is a hydrogen atom, a lower alkyl group or a lower alkoxycarbonyl group, $R_5$ is a lower alkyl group, a lower alkoxy group which may optionally be substituted by hydroxyl, carboxyl or lower alkoxycarbonyl, or a lower alkylamino group which is substituted by hydroxyl, carboxyl or lower alkoxycarbonyl.

2. A pharmaceutical composition according to claim 1, wherein

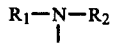

in the formula is the residue of an organic aminocarboxylic acid having a hydrogen atom removed from the amino group thereof.

3. A pharmaceutical composition according to claim 1, wherein $R_3$ in the general formula is a lower alkyl group.

4. A pharmaceutical composition according to claim 3, wherein lower alkyl group is methyl.

5. A pharmaceutical composition according to claim 1, wherein $R_4$ in the general formula is a hydrogen atom.

6. A pharmaceutical composition according to claim 1, wherein $R_5$ in the formula is a group selected from the group consisting of ethoxy, 1-ethoxycarbonylethoxy and 1-glyceryl.

7. A pharmaceutical composition according to claim 1, wherein the enamine derivative is N-(1-methyl-2-ethoxycarbonylvinyl)glycine sodium salt.

8. A pharmaceutical composition according to claim 1, wherein the enamine derivative is N-(1-methyl-2-ethoxycarbonylvinyl)-L-leucine sodium salt.

9. A pharmaceutical composition according to claim 1, wherein the enamine derivative is N-(1-methyl-2-ethoxycarbonylvinyl)-L-phenylglycine sodium salt.

10. A pharmaceutical composition according to claim 1, wherein the enamine derivative is N-(1-methyl-2-ethoxycarbonylvinyl)-DL-phenylglycine sodium salt.

11. A pharmaceutical composition according to claim 1, wherein the enamine derivative is N-[1-methyl-2-(2,3-dihydroxypropoxycarbonyl)vinyl]glycine sodium salt.

12. A pharmaceutical composition according to claim 1, wherein the enamine derivative is N-[1-methyl-2-(1-ethoxycarbonyl-ethoxycarbonyl)vinyl]glycine sodium salt.

13. A pharmaceutical composition according to claim 1, wherein digestive tract is rectum.

* * * * *